United States Patent
Kitasaka et al.

(10) Patent No.: US 7,241,625 B2
(45) Date of Patent: Jul. 10, 2007

(54) CARBONYL COMPOUND SCAVENGER AND METHOD OF QUANTIFYING CARBONYL COMPOUND USING THE SAME

(75) Inventors: Kazuya Kitasaka, Osaka (JP); Hatsumi Shimajiri, Osaka (JP); Koichi Sugihara, Osaka (JP)

(73) Assignee: Sumika Chemical Analysis Service, Limited, Osaka (JP)

( * ) Notice: Subject to any disclaimer, the term of this patent is extended or adjusted under 35 U.S.C. 154(b) by 0 days.

(21) Appl. No.: 11/142,372

(22) Filed: Jun. 2, 2005

(65) Prior Publication Data

US 2006/0275913 A1 Dec. 7, 2006

(51) Int. Cl.
C07C 255/50 (2006.01)

(52) U.S. Cl. .............................. 436/128; 558/422

(58) Field of Classification Search ................ 558/422; 436/128

See application file for complete search history.

(56) References Cited

U.S. PATENT DOCUMENTS 5,120,849 A * 6/1992 Wild et al. .................. 546/334

FOREIGN PATENT DOCUMENTS

| JP | 2002-195990 A | | 7/2002 |
| JP | 2002195990 A | * | 7/2002 |
| WO | WO 2005054179 A2 | * | 6/2005 |

OTHER PUBLICATIONS

Waters, high performance liquid chromatography column consumable articles general catalogue 2002, cep pack for atmosphere, DNPH/ozone scrubber, p. 20, Nippon Waters K.K.

2001 Chromatography article catalogue, pp. 78-80, Sigma Aldrich Japan K.K., Aug. 2001.

Y. Mori et al., Journal of Environmental Chemistry, vol. 7, No. 3, pp. 515-520, 1997.

* cited by examiner

Primary Examiner—Kamal A. Saeed
Assistant Examiner—Joseph R. Kosack
(74) Attorney, Agent, or Firm—Birch, Stewart, Kolasch & Birch, LLP (57) ABSTRACT

A carbonyl compound scavenger comprising a mineral acid salt of a benzylhydroxyamine-based compound of the formula (1) and at least one adsorbent selected from the group consisting of silica gel, alumina, cellulose and activated carbon:

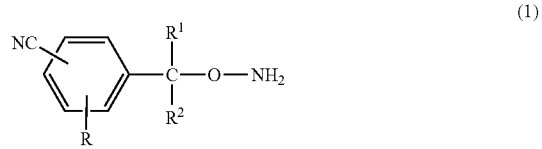

(1)

[wherein, R represents an alkyl group having 1 to 8 carbon atoms, haloalkyl group having 1 to 4 carbon atoms, alkoxy group having 1 to 4 carbon atoms, haloalkoxy group having 1 to 4 carbon atoms, nitro group or cyano group, and $R^1$ and $R^2$ represent each independently a hydrogen atom or alkyl group having 1 to 8 carbon atoms, and a hydrogen atom on a benzene ring to which a cyano group and R are connected may be substituted with an alkyl group having 1 to 8 carbon atoms, haloalkyl group having 1 to 4 carbon atoms, alkoxy group having 1 to 4 carbon atoms, haloalkoxy group having 1 to 4 carbon atoms, aryl group having 6 to 10 carbon atoms, nitro group or cyano group.].

7 Claims, 2 Drawing Sheets

CARBONYL COMPOUND SCAVENGER AND METHOD OF QUANTIFYING CARBONYL COMPOUND USING THE SAME

TECHNICAL FIELD OF THE INVENTION

The present Invention relates to a carbonyl compound scavenger used for collecting a carbonyl compound of aldehydes and ketones, and a method of quantifying a carbonyl compound using the scavenger.

BACKGROUND OF THE INVENTION

Recently, there is a social problem of an influence on environments by a carbonyl compound of aldehydes such as formaldehyde, acetaldehyde, acrolein and the like and ketones such as acetone, methyl ethyl ketone and the like in water and atmosphere, and particularly, an influence by a carbonyl compound diffused from building materials, furniture and the like on dwelling environments and working environments due to air tightness of dwelling houses, or the like constitutes a social problem. For investigating a countermeasure for such a problem, it is necessary to measure the quantity of a carbonyl compound in atmosphere, and development of a method capable of simply measuring the quantity of a carbonyl compound in atmosphere in room and the like is desired.

Regarding the method of quantifying a carbonyl compound, a carbonyl compound scavenger obtained by coating silica gel with 2,4-dinitrophenylhydrazine (hereinafter, referred to as DNPH in some cases) is disclosed in "Waters, high performance liquid chromatography column-consumable articles general catalogue 2002cep pack for atmosphere, DNPH/ozone scriber, page 20, Nippon Waters K.K." and "2001 chromatography article catalogue, pp. 78 to 80. Sigma Aldrich Japan K.K., published on August, 2001" and it is disclosed that this scavenger collects a carbonyl compound to form a reaction substance of DNPH with a carbonyl compound, then, the scavenger is washed with an organic solvent, resultantly, the reaction substance is eluted, and can be quantified by gas chromatography or liquid chromatography.

Further, regarding the quantification method using a compound other than hydrazine, a quantification method using a carbonyl compound scavenger obtained by impregnating silica gel with O-(2,3,4,5,6-pentafluorobenzyl)hydroxyamine (hereinafter, referred to as PFBOA in some cases) and phosphoric acid is reported in "Yasuaki Mori et al., Environmental Chemistry, vol. 7pp. 515 to 520 (1997)" and also the present inventors have reported that a mineral acid salt of an O-(haloalkoxybenzyl)hydroxyamine-based compound, specifically, an O-(4-trifluoromethoxybenzyl) hydroxyamine hydrochloride is allowed to be retained on a cation exchanger to produce a carbonyl compound scavenger, and this scavenger collects a carbonyl compound to form an imine compound of the hydrochloride with a carbonyl compound, then, the scavenger is washed with an organic solvent, resultantly, the imine compound is eluted and can be quantified by a gas chromatography mass spectrometer (GO/MS) (Japanese Patent Application Laid-Open (JP-A) No. 2002-195990).

The present inventors have investigated a scavenger using DNPH and clarified that since it is extremely excellent in reactivity with a carbonyl compound, it can quantify a carbonyl compound of low concentration, however, it reacts with a trace amount of carbonyl compound present in air In atmosphere or room even before measurement such as in production of the scavenger and the like, to provide dispersed blank value before measurement, consequently, there is a problem that it is difficult to correctly measure a carbonyl compound of low concentration unless quantification is effected using a lot of scavengers.

Further, the present inventors have sampled an air sample in general dwelling environments of approximately 25 to 30° C. using the above-mentioned scavenger containing PFBOA instead of DNPH, to resultantly clarify that formaldehyde can be collected only approximately 70 to 77% as compared with a scavenger containing DNPH and a carbonyl compound cannot be collected sufficiently in some cases even if a carbonyl compound scavenger containing PFBOA is used, under high temperature such as in summer and the like.

Furthermore, it has been clarified that an imine compound composed of an O-(4-trifluoromethoxybenzyl)hydroxyamine hydrochloride and a carbonyl compound does not have a UV absorption peak of 240 nm, and it is difficult to quantify the compound by liquid chromatography using a generally used UV detector.

DETAILED DESCRIPTION OF THE INVENTION

An object of the present invention is to provide a carbonyl compound scavenger having simultaneously reproducibility capable of eliminating an influence of a carbonyl compound of low concentration reacting before measurement, to reduce dispersion in measured value, correctness capable of correctly quantifying a carbonyl compound of low concentration in measurement, heat resistance capable of quantifying a carbonyl compound of low concentration even under high temperature, and simplicity capable of quantifying by generally used liquid chromatography having a UV absorption peak at 240 nm, and a quantification method using this scavenger.

The present inventors have studied to find a carbonyl compound scavenger scarcely manifesting the problems as described above and resultantly found that a scavenger containing a mineral acid salt of a benzylhydroxyamine-based compound and a certain adsorbent is excellent in reproducibility, correctness and heat resistance and also has simplicity.

Namely, the present invention provides the following [1] to [9].

[1] A carbonyl compound scavenger comprising a mineral acid salt of a benzylhydroxyamine-based compound of the formula (1) and at least one adsorbent selected from the group consisting of silica gel, alumina, cellulose and activated carbon:

(1)

[wherein, R represents an alkyl group having 1 to 8 carbon atoms, haloalkyl group having 1 to 4 carbon atoms, alkoxy group having 1 to 4 carbon atoms, haloalkoxy group having 1 to 4 carbon atoms, nitro group or cyano group, and $R^1$ and $R^2$ represent each independently a hydrogen atom or alkyl group having 1 to 8 carbon atoms, and a hydrogen atom on a benzene ring to which a cyano group and R are connected may be substituted with an alkyl group having 1 to 8 carbon atoms, haloalkyl group having 1 to 4 carbon atoms, alkoxy group having 1 to 4 carbon atoms, haloalkoxy group having 1 to 4 carbon atoms, aryl group having 6 to 10 carbon atoms, nitro group or cyano group.].

[2] A carbonyl compound scavenger obtained by compounding a benzylhydroxyamine-based compound of the formula (1), a mineral acid salt and at least one adsorbent selected from the group consisting of silica gel, alumina, cellulose and activated carbon:

(1)

[wherein, R represents an alkyl group having 1 to 8 carbon atoms, haloalkyl group having 1 to 4 carbon atoms, alkoxy group having 1 to 4 carbon atoms, haloalkoxy group having 1 to 4 carbon atoms, nitro group or cyano group, and $R^1$ and $R^2$ represent each independently a hydrogen atom or alkyl group having 1 to 8 carbon atoms, and a hydrogen atom on a benzene ring to which a cyano group and R are connected may be substituted with an alkyl group having 1 to 8 carbon atoms, haloalkyl group having 1 to 4 carbon atoms, alkoxy group having 1 to 4 carbon atoms, haloalkoxy group having 1 to 4 carbon atoms, aryl group having 6 to 10 carbon atoms, nitro group or cyano group.].

[3] The carbonyl compound scavenger according to [1] or [2], wherein the mineral acid is phosphoric acid.

[4] The carbonyl compound scavenger according to any one of [1] to [3], wherein the adsorbent is silica gel for chromatography.

[5] A collecting tube comprising a vessel having air permeability filled with the carbonyl compound scavenger according to any one of [1] to [4].

[6] A carbonyl compound quantification kit comprising the collecting tube according to [5] sealed with a non-air permeable material.

[7] A method for quantifying a carbonyl compound comprising the steps of;

washing the scavenger according to any one of [1] to [4] with at lease one hydrophilic solvent selected from the group consisting of lower aliphatic nitriles, lower alcohols, lower aliphatic ethers and lower cyclic ethers, drying this, allowing a sample containing a carbonyl compound of the formula:

$R^3C(=O)R^4$

[wherein, $R^3$ and $R^4$ represent each independently a hydrogen atom, alkyl group having 1 to 8 carbon atoms, alkenyl group having 1 to 8 carbon atoms or aryl group having 6 to 10 carbon atoms.] to permeate through the resulted scavenger to adsorb the carbonyl compound as a derivative of the formula (2), subsequently, washing with a hydrophilic solvent to elute the derivative (2), and quantifying the derivative (2) in the resulting washing liquid:

(2)

[wherein, R, $R^1$, $R^2$, $R^3$ and $R^4$ represent the same meanings as described above.].

[8] A cyano group-containing benzylhydroxyamine compound of the formula (1) as described above.

[9] An imine compound of the formula (2) as described above.

BRIEF EXPLANATION OF DRAWINGS

FIG. 2 (1) shows a chart of elution liquid from a carbonyl compound scavenger containing silica gel and a salt composed of phosphoric acid and O-(4-cyano-2-ethoxybenzyl)hydroxyamine (18) and FIG. 2 (2) shows a chart of each derivative of O-(4-cyano-2-ethoxybenzyl)hydroxyamine (18) contained in an amount of 0.5 µg/ml as a concentration of formaldehyde, acetaldehyde, acetone and acrolein in a sample.

FIG. 3 (1) shows a chart of elution liquid from DNPH sampler short body (formaldehyde scavenger manufactured by Waters, containing 2,4-dinitrophenylhydrazine (DNPH)) and FIG. 3 (3) shows a chart of each derivative of DNPH contained in an amount of 0.5 µg/ml as a concentration of formaldehyde, acetaldehyde and acetone in a sample.

EXPLANATION OF SYMBOLS

1: carbonyl compound collecting tube
2: vessel (made of polyethylene)
3: carbonyl compound scavenger
4: polypropylene filter
5: suction port
11: formaldehyde
12: acetaldehyde
13: acetone
14: acrolein
15: O-(4-cyano-2-ethoxybenzyl)hydroxyamine
16: 2,4-dinitrophenylhydrazine (DNPH)
(1): blank chart (chart in the case of no collecting)
(2) chart of each derivative of O-(4-cyano-2-ethoxybenzyl)hydroxyamine (18) contained in an amount of 0.5 µg/ml as a concentration of formaldehyde, acetaldehyde, acetone and acrolein In a sample.
(3) chart of each derivative of 2,4-dinitrophenylhydrazine (DNPH) contained in an amount of 0.5 µg/ml as a concentration of formaldehyde, acetaldehyde and acetone in a sample.

The present invention will be illustrated in detail below.

The adsorbent used in the present invention is at least one adsorbent selected from the group consisting of silica gel, alumina, cellulose and activated carbon.

As the silica gel, used are silica gels in the form of particle and powder containing main components having particle sizes of usually 10 to 500 µm, preferably approximately 40 to 300 µm. Specifically, commercially available silica gels for chromatography are used such as silica gel manufactured by Kanto Kagaku K. K., silica gel manufactured by Fuji Silysia Chemical Ltd., silica gel manufactured by Merck, silica gel manufactured by Sigma Aldrich, and the like. Of them, neutrally controlled silica gels are preferably used.

As the alumina, active aluminas in the form of particle and powder are usually used. Specifically, commercially available active aluminas for chromatography are exemplified such as aluminum oxide 90 active type basic manufactured by Merck, active aluminas A11 and AC-11 manufactured by Sumitomo Chemical Co., Ltd., and the like.

As the cellulose, celluloses in the form of particle and powder are usually used, and specifically, KC Flock (manufactured by Sanyo Kokusaku Pulp K.K.) and the like are exemplified.

As the activated carbon, activated carbons in the form of particle and powder are used, and activated carbons for catalyst carrier are suitably used.

Further, as the adsorbent, different adsorbents may be used together, and for example, activated carbon mixed silica gel and the like may be used.

The adsorbent used in the present invention does not contain a cation exchange group such as a sulfonyl group, carboxyl group, phosphate group and the like. Namely, it is a different adsorbent from the adsorbent containing a cation exchange group such as silica gel containing an introduced benzensulfonyl group, carboxylmethylcellulose, cellulose containing an introduced sulfoethyl group, and the like.

R in the benzylhydroxyamine-based compound (1) used in the present invention represents an alkyl group having 1 to 8 preferably 1 to 4 carbon atoms such as a methyl group, ethyl group and the like; alkoxy group having 1 to 4 carbon atoms such as a methoxy group, ethoxy group and the like; haloalkyl group composed of an alkyl group having 1 to 4 carbon atoms and a halogen atom such as chlorine, fluorine and the like such as a trifluoromethyl group and the like; haloalkoxy group having 1 to 4 carbon atoms such as a trifluoromethoxy group and the like; nitro group or cyano group.

A hydrogen atom on a benzene ring to which a cyano group and R are connected in the benzylhydroxyamine-based compound (1) maybe substituted with an alkyl group having 1 to 8 preferably 1 to 4 carbon atoms; haloalkyl group composed of an alkyl group having 1 to 4 carbon atoms and a halogen atom such as chlorine, fluorine and the like; alkoxy group having 1 to 4 carbon atoms; haloalkoxy group having 1 to 4 carbon atoms; aryl group having 6 to 10 carbon atoms such as a phenyl group, benzyl group and the like; nitro group; or cyano group.

$R^1$ and $R^2$ in the benzylhydroxyamine-based compound (1) represent each independently a hydrogen atom or alkyl group having 1 to 8 carbon atoms, and particularly, it is preferable all of them are a hydrogen atom.

As the benzylhydroxyamine-based compound (1), exemplified are O-(4-cyanobenzyl)hydroxylamine, O-(4-cyano-2-nitrobenzyl)hydroxylamine, O-(4-cyano-2-methoxybenzyl)hydroxylamine, O-(4-cyano-2-ethoxybenzyl) hydroxylamine, O-(4-cyano-2-isopropoxybenzyl) hydroxylamine and the like, and among compounds (1) having a cyano group, compounds in which R represents an alkoxy group are preferable, and O-(4-cyano-2-methoxybenzyl)hydroxylamine and O-(4-cyano-2-ethoxybenzyl)hydroxylamine are particularly suitable.

Regarding the method of producing a benzylhydroxyamine-based compound (1), in the case of for example O-(4-cyano-2-ethoxybenzyl)hydroxylamine, there is mentioned a method for synthesis thereof from cyanotoluene via cyanocresol (14) into which a corresponding alkoxy group can be easily introduced, or the like.

When a mineral acid salt (for example, the formula (19) represents a hydrochloride of O-(4-cyano-2-ethoxybenzyl) hydroxylamine) obtained by further reacting a mineral acid to the formula (18) is used, it can be easily purified by re-crystallization. Therefore, a method is recommended in which after production of a benzylhydroxyamine-based compound (1) as shown in the formula (18), it is purified as a mineral acid salt of a benzylhydroxyamine-based compound (1) rather than immediate use thereof, then, it is neutralized with ammonia water or the like, to give a benzylhydroxyamine-based compound (1) to be used.

-continued

19

The benzylhydroxyamine-based compound (1) is from the standpoint of easy handling, usually mixed with a hydrophilic solvent, and used as a solution having a concentration of the compound (1) of 1 to 30 wt %. When the solution is 1 wt % or more. mixing tends to be easy preferably, and when 30 wt % or less, solubility of the compound (1) tends to be excellent preferably.

Here, as the hydrophilic solvent, exemplified are lower aliphatic nitriles, lower alcohols, lower aliphatic ethers and lower cyclic ethers. In the instant specification, the lower aliphatic nitrile means an aliphatic nitrile having 6 or less carbon atoms, for example, acetonitrile and the like, the lower alcohol means an alcohol having 5 or less carbon atoms, for example, methyl alcohol, ethyl alcohol and the like, the lower aliphatic ether means an aliphatic ether having 10 or less carbon atoms, and the lower cyclic ether means a cyclic ether having 6 or less carbon atoms, for example, tetrahydrofuran and the like. Of these hydrophilic solvents, acetonitrile, methyl alcohol and the like are preferable, and acetonitrile is particularly preferable.

The use amount of the benzylhydroxyamine-based compound (1) is usually from approximately 0.01 to 5 parts by weight, preferably from approximately 0.2 to 2.5 parts by weight based on 100 parts by weight of an adsorbent. When 0.01 part by weight or more, a carbonyl compound tends to be collected sufficiently preferably, and when 5 parts by weight or less, a blank value tends to be maintained low preferably.

As the mineral acid used in the present invention, hydrochloric acid, nitric acid, sulfuric acid, phosphoric acid and the like are mentioned, and of them, a carbonyl compound scavenger using phosphoric acid tends to be excellent in storage stability, reactivity and collecting efficiency, therefore, phosphoric acid is preferable as the mineral acid.

A mineral acid salt of a benzylhydroxyamine-based compound (1) can be obtained, for example, by charging a compound (1) and a solvent in a reaction vessel, blowing a halogen gas such as a hydrochloric acid gas and the like, and stirring them.

A mineral acid salt of a benzylhydroxyamine-based compound (1) contained in a carbonyl compound scavenger can also be produced by, for example, dropping a mineral acid such as phosphoric acid and the like into a reaction vessel charged with a benzylhydroxyamine-based compound (1), adsorbent and solvent, and stirring them.

The use amount of a mineral acid is usually approximately 2 to 50 mol, preferably approximately 5 to 20 mol per mol of a benzylhydroxyamine-based compound (1). When 2 mol or more, a benzylhydroxyamine-based compound (1) tends to be converted sufficiently into a salt of a mineral acid preferably, and when 50 mol or less, corrosion of an adsorbent tends to be reduced preferably.

From the standpoint of easy handling of a mineral acid, an aqueous solution of a mineral acid is usually used as a solution mixed with a hydrophilic solvent. Specifically, in the case of for example phosphoric acid, it may be advantageous that a hydrophilic solvent is mixed in a phosphoric acid aqueous solution of approximately 50 to 90 wt % to give a solution of 5 to 20 wt %. When an aqueous solution of a mineral acid is handled as a mineral acid aqueous solution of high concentration in the range of easy handling, impurities such as formaldehyde, acetaldehyde and the like derived from water tend to be reduced preferably.

The carbonyl compound scavenger of the present invention comprises a mineral acid salt of a benzylhydroxyamine-based compound (1) and the above-mentioned adsorbent. As the method of producing a carbonyl compound scavenger, there are mentioned, for example, (i) a method in which a solution of the above-mentioned compound (1) is mixed with an adsorbent previously washed with a hydrophilic solvent and dried, the mixture is stirred for approximately 0.5 to 120 minutes, preferably 5 to 60 minutes, subsequently, the above-mentioned mineral acid solution is added and the mixture is stirred for approximately 0.5 to 5 hours, then, filtrated and dried, (ii) a method in which an adsorbent filled in a column and the like is washed with a hydrophilic solvent, then, a solution of the above-mentioned compound (1) is circulated in the column and performed until the quantity of the compound (1) does not decrease from the solution discharged from the column, then, a mineral acid solution is circulated under the same condition, (iii) a method in which a hydrophilic solvent for a benzylhydroxyamine-based compound (1) and a mineral acid solution are mixed to obtain a solution or crystal of a mineral acid salt of the benzylhydroxyamine-based compound (1), which is mixed with an adsorbent, and other methods. Of them, the method (i) is preferable since a large amount of carbonyl compound scavenger can be treated simply and in a short period of time,

It is preferable that thus obtained carbonyl compound scavenger is a material in which a mineral acid salt of a benzylhydroxyamine-based compound (1) is adsorbed or carried on an adsorbent.

Specifically exemplified of the method of quantifying a carbonyl compound is a method in which, first, a carbonyl compound scavenger is washed with a hydrophilic solvent and dried under a clear condition such as under reduced pressure and the like, then, a carbonyl compound of the following formula:

$$R^3C(=O)R^4$$

[wherein, $R^3$ and $R^4$ represent each independently a hydrogen atom, alkyl group having approximately 1 to 8 carbon atoms, alkenyl group having approximately 1 to 8 carbon atoms or aryl group having 6 to 10 carbon atoms.]

contained In an atmosphere sample or water sample is allowed to contact a carbonyl compound scavenger of the present invention to obtain a derivative of the formula (2):

(2)

[wherein, R, $R^1$, $R^2$, $R^3$ and $R^4$ represent the same meanings as described above.], the carbonyl compound scavenger containing this derivative is washed with a hydrophilic solvent to elute a derivative (2), and the washing liquid containing the resulted derivative (2)

is analyzed by gas chromatography such as capillary GC/MS and the like, liquid chromatography and the like, to quantify a carbonyl compound, or other method.

Here, by washing a scavenger before collecting a carbonyl compound, a reaction substance with a carbonyl compound mixed in production of a scavenger and the like can be eluted and dispersion in measured value can be remarkably reduced, therefore, quantification excellent in correctness and excellent in reproducibility can be performed on a carbonyl compound having low concentration. Since an unreacted mineral acid salt of a benzylhydroxyamine-based compound (1) in a carbonyl compound scavenger of the present invention Is not eluted by a hydrophilic solvent, it can be subjected to the quantification of a carbonyl compound. The above-mentioned washing and drying may be performed immediately before measurement, however, for example, when a carbonyl compound scavenger is filled in a collecting tube, it is preferable to perform washing and drying after production of a collecting tube, then, seal the tube with a non-air permeable material such as an aluminum laminate bag, can and the like, and use the resulted carbonyl compound quantification kit, since handling is easy and, additionally, pollution is not caused so as to generate a problem of dispersion in measured value.

For washing of a scavenger, a hydrophilic solvent is used usually in an amount of approximately 5 to 20 parts by weight per one part by weight of a carbonyl compound scavenger once or twice. By the above-mentioned amount and number of times, a collection tube showing little dispersion in measured value can be obtained.

Specific examples of a carbonyl compound [$R^3C(=O)R^4$] which can be quantified in the present invention include formaldehyde, acetaldehyde, acetone, acrolein, crotonaldehyde, butanone, valeraldehyde, benzaldehyde, propionaldehyde and the like.

As the specific method of quantifying a carbonyl compound [$R^3C(=O)R^4$], there is mentioned, for example, a method in which a carbonyl compound is collected from an air sample using a collecting tube comprising a vessel having air permeability filled with a carbonyl compound scavenger, then, a derivative (2) is removed from the collecting tube and quantified, or the like.

Specifically, a quantification method using an active sampler as the collecting tube will be illustrated below as a typical example. First, a collecting tube as a tubular vessel having an internal diameter of approximately 3 to 15 mm and a length of approximately 1 to 10 cm is filled with a carbonyl compound scavenger to an extent of sufficient flowing of an air sample, and plugged with a filter capable of retaining a carbonyl compound scavenger. Next, the product is washed with a hydrophilic solvent and dried to prepare a carbonyl compound collecting tube. The collecting tube is usually preserved under close sealing. Then, the close sealing is liberated under an air sample atmosphere, and a pump is connected and an air sample is acquired at a suction rate of the pump of approximately 0.01 to 1.5 l/min. Subsequently, the collecting tube is washed with a hydrophilic solvent to obtain a solution containing the derivative (2) and hydrophilic solvent. Finally, the solution is analyzed by liquid chromatography, gas chromatography and the like.

In addition to the quantification method using an active sampler acquiring an air sample by a pump as described above, there are exemplified a method In which a collecting tube of which total body or main portion thereof has air permeability such as a porous tube and the like is filled with a carbonyl compound scavenger to prepare a collecting tube, and the collecting tube is left stationarily in an air sample to acquire the sample and the sample is quantified in the same manner, namely, a quantification method by a passive sampler and the like.

Regarding the gas chromatography, analysis with good precision is possible by conducting analysis by a capillary GC/MS method and the like, and simple analysis is possible by generally used liquid chromatography equipped with an UV detector.

For quantifying a carbonyl compound, it may be advantageous that a carbonyl compound and a benzylhydroxyamine-based compound (1) are previously reacted to prepare a derivative (2) separately, and it is quantified by an absolute calibration curve method, internal standard method and the like using the above-mentioned chromatography.

If a carbonyl compound scavenger of the present invention is washed with a hydrophilic solvent such as acetonitrile and the like before using the carbonyl compound scavenger of the present invention, a derivative of a carbonyl compound of low concentration mixed in production is eluted, therefore, it is possible to exclude an influence of a carbonyl compound of low concentration mixed before measurement to reduce dispersion in measured value and to correctly quantify a carbonyl compound having low concentration excellent in reproducibility.

The carbonyl compound scavenger of the present invention can perform quantification also on an air sample containing a carbonyl compound of low concentration at approximately the same extent as a scavenger containing DNPH, particularly, on formaldehyde and acetaldehyde, can perform quantification further excellent in reproducibility and correctness, and also on a compound such as acrolein, acetone and the like of low concentration, can perform quantification excellent in reproducibility and correctness.

Further, since an imine compound obtained from a compound of the formula (2) and a carbonyl compound has a UV absorption at 240 nm, quantification can be effected simply by generally used liquid chromatography.

Of them, it is stable in a collecting tube not only at room temperature of 25° C. but also at high temperatures of approximately 80° C., and it can be used also at high temperatures.

Since the carbonyl compound scavenger of the present invention has reproducibility, correctness, heat resistance and simplicity, it can perform micro analysis of carbonyl compounds of aldehydes such as formaldehyde, acetaldehyde, acrolein and the like and ketones such as acetone, methyl ethyl ketone and the like contained in airs in house room, building, factory, waste disposal factory and the like, air under natural environments, high temperature gas samples such as a discharge gas of automobiles, and liquid samples such as water and sewerage, river, marine water, industrial drainage and the like.

EXAMPLES

The present invention will be specifically illustrated by examples below, but the present invention is not limited to these examples.

Production Example of benzylhydroxyamine-based compound (1)

Synthesis Example of 4-cyano-2-nitrotoluene (12)

Into a reaction vessel was charged fuming nitric acid (300 ml, 7.2 mol) and 4-cyanotoluene (11) (120.0 g, 1.02 mol) was dropped on this under freezing point, and stirred for 1 hour at this condition. Ice water was added to the reaction mixture and the precipitated pale yellow solid was filtrated. This was air-dried to obtain water-containing 4-cyano-2-nitrotoluene (12) (300 g).

$^1$H-NMR (δ, ppm, CDCl$_3$) . . . 2.70 (3H, s), 7.52 (1H, d), 7.79 (1H, dd), 8.28 (1H, d)

Synthesis Example of 4-cyano-2-aminotoluene (13)

Into a reaction vessel was charged 4-cyano-2-nitrotoluene (12) (300 g) and ethanol, and 10% palladium/carbon (9.5 g) was added to this and a hydrogen catalytic reduction reaction was conducted at room temperature. When absorption of hydrogen disappeared, palladium/carbon was removed by filtration, then, the solvent was distilled off from filtrate, to obtain 4-cyano-2-aminotoluene (13) (132.5 g, yield from (11) is 98%).

$^1$H-NMR (δ, ppm, CDCl$_3$) . . . 2.00 (3H, s), 3.81 (2H, brs), 6.89 (1H, d), 6.97 (1H, dd), 7.10 (1H, d)

Synthesis Example of 4-cyano-2-hydroxytoluene (14)

Into a reaction vessel was charged 4-cyano-2-aminotoluene (13) (132.0 g, 1.0 mol) and 6 N hydrochloric acid aqueous solution (800 ml), and an aqueous solution obtained by dissolving ice-cooled sodium nitrite (76.0 g, 1.1 mol) in water (320 ml) was dropped over 1.5 hours, further, the solution was stirred for approximately 20 hours under ref lux. To the reaction liquid was added toluene and extracted, then, a sodium hydroxide aqueous solution was added to the toluene layer to make the aqueous layer alkaline. The resulted aqueous layer was acidified with concentrated hydrochloric acid, then, extracted with ethyl acetate. The resulted ethyl acetate layer was washed with saturated saline, dried, and the solvent was distilled off under reduced pressure, to obtain 4-cyano-2-hydroxytoluene (14) (91.6 g, yield from (13) is 69%).

$^1$H-NMR (δ, ppm, CDCl$_3$) . . . 2.31 (3H, s), 6.25 (1H, s), 7.05 to 7.22 (3H, m)

Synthesis Example of 4-cyano-2-ethoxytoluene (15)

Into a reaction vessel was charged sodium hydride (4.8 g, 0.12 mol) and N,N'-dimethylformamide (40 ml), and a solution obtained by dissolving 4-cyano-2-hydroxytoluene (14) (13.3 g, 0.1 mol) in N,N'-dimethylformamide (40 ml) in an ice bath was dropped on this, and the solution was stirred for 1.0 hour at room temperature. Subsequently, ethyl iodide (18.7 g, 0.12 mol) was dropped in an ice water, and the solution was stirred for 1.5 hours at room temperature. To the reaction liquid was added water and extracted with ethyl acetate, then, washed with saturated saline, dried, and the solvent was distilled off under reduced pressure, to obtain 4-cyano-2-ethoxytoluene (15) (16.1 g, yield from (14) is 99%).

$^1$H-NMR (δ, ppm, CDCl$_3$) . . . 1.45 (3H, t), 2.26 (3H, s), 4.04 (2H, q), 7.00 (1H, s), 7.14 (1H, d), 7.19 (1H, d)

Synthesis Example of 4-cyano-2-ethoxy-α-bromotoluene (16)

Into a reaction vessel was charged 4-cyano-2-ethoxytoluene (15) (16.0 g, 0.1 mol) and 1,2-dichloroethane (160 ml), and 2,2'-azobis(isobutyronitrile) (800 mg) and N-bromosuccinic imide (19.4 g, 0.11 mol) were added to this, and the mixture was stirred for 1 hour at 80 to 90° C. Hexane was added to the reaction liquid and the precipitated solid was filtrated. The resulted filtrate was concentrated, to obtain 4-cyano-2-ethoxy-α-bromotoluene (16) (20.3 g, yield from (15) is 85%).

$^1$H-NMR (δ, ppm, CDCl$_3$) . . . 1.50 (3H, t), 4.12 (2H, q), 4.52 (2H, s), 7.09 (1H, d), 7.21 (1H, dd), 7.42 (1H, d)

Synthesis Example of N-(4-cyano-2-ethoxybenzyloxy)phthalimide (17)

Into a reaction vessel was charged 4-cyano-2-ethoxy-α-bromotoluene (16) (20.2 g, 0.084 mol) and N,N'-dimethylformamide (200 ml), and N-hydroxyphthalimide (14.4 g, 0.088 mol) and anhydrous potassium carbonate (12.2 g, 0.088 mol) were added to this, and the mixture was stirred for 2 hours at approximately 80° C. Water was added to the reaction liquid and the precipitated solid was filtrated. This was dried, to obtain N-(4-cyano-2-ethoxybenzyloxy)phthalimide (17) (27.0 g, yield from (16) is 99%).

$^1$H-NMR (δ, ppm, CDCl$_3$) . . . 1.39 (3H, t), 4.02 (2H, q), 5.31 (2H, s), 7.07 (1H, s), 7.27 (1H, d), 7.65 (1H, d), 7.72 to 7.84 (4H, m)

Synthesis Example of O-(4-cyano-2-ethoxybenzyl)hydroxyamine (18)

Into a reaction vessel was charged N-(4-cyano-2-ethoxybenzyloxy)phthalimide (17) (27.0 g, 0.084 mol) and ethanol (270 ml), and hydrazine monohydrate (4.6 g, 0.091 mol) were added, and the mixture was stirred for 2 hours at approximately 80° C. The precipitated white solid was removed by filtrated, and the resulted filtrate was subjected to reduce pressure to distill off the solvent. Next, ethyl acetate was added and the mixture was washed with a dilute sodium carbonate aqueous solution, dried over anhydrous magnesium sulfate, then, the solvent was distilled off under reduced pressure, to obtain O-(4-cyano-2-ethoxybenzyl)hydroxyamine (18) (13.4 g, yield from (17) is 83%).

$^1$H-NMR (δ, ppm, CDCl$_3$) . . . 1.45 (3H, t), 4.06 (2H, q), 4.79 (2H, s), 5.54 (2H, brs), 7.07 (1H, d), 7.26 (1H, dd), 7.45 (1H, d)

Production Example of Salt of benzylhydroxyamine-based compound (1) and Mineral Acid Synthesis Example of O-(4-cyano-2-ethoxybenzyl)hydroxyamine hydrochloride (19)

Into a reaction vessel was charged O-(4-cyano-2-ethoxybenzyloxy)hydroxyamine (18) (13.4 g, 0.042 mol) and diethyl ether (260 ml), and a hydrochloric acid gas was blown, and the solution was stirred for 0.5 hours. The precipitated white solid was filtrated, and the filtrated substance was washed with diethyl ether, then, dried. Re-crystallization was conducted by a mixed solvent of water and acetonitrile, to obtain O-(4-cyano-2-ethoxybenzyl)hydroxyamine hydrochloride in the form white needle-shaped crystal (19) (11.3 g, yield from (18) is 71%).

$^1$H-NMR (δ, ppm, D$_2$O) . . . 1.42 (3H, t), 4.17 (2H, g), 5.15 (2H, s), 7.40 (1H. d), 7.42 (1H, s), 7.53 (1H, d)

Production Example of Carbonyl Compound Scavenger Containing O-(4-cyano-2-ethoxybenzyl)hydroxyamine (18), Phosphoric Acid and Silica Gel The O-(4-cyano-2-ethoxybenzyl)hydroxyamine hydrochloride (19) obtained above and ammonia water were mixed, then, extracted with diethyl ether, then, dried and the solvent was distilled off. To the resulted concentrated substance was added acetonitrile to obtain an acetonitrile (20 ml) solution containing O-(4-cyano-2-ethoxybenzyl)hydroxyamine (18) (476 mg, 2.5 mmol).

Into another reaction vessel was charged silica gel (100 g, manufactured by Kanto Kagaku K. K., 60 N, neutral, spherical, 63 to 210 µm) and acetonitrile (300 ml), the mixture was stirred for a while, and filtrated to remove acetonitrile. Subsequently, to the resulted washed silica gel was added acetonitrile (200 ml), and the above-mentioned acetonitrile solution containing (18) was dropped on this, and the mixture was stirred for 10 minutes at room temperature. Then, a mixture solution of phosphoric acid (3 0 g, 25.8 mmol) and acetonitrile (20 ml) was dropped, and the mixture was stirred for 1 hour at room temperature. The reaction liquid was filtrated to remove acetonitrile, further, the filtrated substance was washed with acetonitrile. The filtrated substance was recovered and dried, to obtain 102.2 g of a carbonyl compound scavenger.

Phosphate of O-(4-cyano-2-ethoxybenzyl)hydroxyamine (18)

The O-(4-cyano-2-ethoxybenzyl)hydroxyamine hydrochloride (19) and ammonia water were mixed, then, extracted with ethyl acetate to obtain O-(4-cyano-2-ethoxybenzyl)hydroxyamine (18) (80 mg, 0.42 mmol). This was dissolved in acetonitrile (12 ml), then, several drops of 85% phosphoric acid aqueous solution were dropped on this, and the produced white solid was filtrated by filtration under reduced pressure. The filtrated substance was washed with acetonitrile, then, the filtrated substance was recovered and dried by a vacuum pump to obtain 60 mg of a while solid.

Production Example of Carbonyl Compound Collecting Tube

Figure 1:
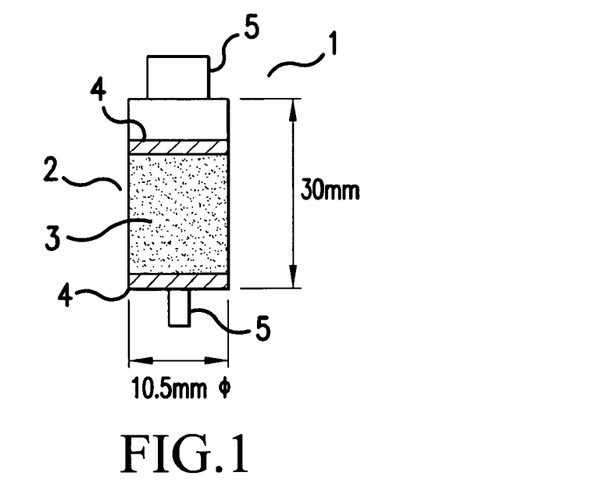
FIG. 1 shows a carbonyl compound collecting tube used in examples of the present invention.

A vessel made of polyethylene having an internal diameter of 10.5 mm and a length of 30 mm as shown in FIG. 1 was filled with the above-mentioned carbonyl compound scavenger (420 mg). The vessel was plugged with a polypropylene filter (fine pore diameter 50 µm) and the scavenger was retained. This was washed with acetonitrile (5 ml) in a glove box under nitrogen flow, dried at approximately 40° C. for 4 hours by a vacuum pump, to obtain a carbonyl compound collecting tube. Upper and lower suction ports were closely sealed, further, the tube was packed in an aluminum laminate bag and closely sealed.

Through the collecting tube, acetonitrile/28% ammonia water=100/3 (10 ml) was passed to elute O-(4-cyano-2-ethoxybenzyl)hydroxyamine (18), and quantified under the following conditions, as a result, elution of 2 mg was observed, that is, approximately the theoretical amount of O-(4-cyano-2-ethoxybenzyl)hydroxyamine (18) was contained in the carbonyl compound collecting tube.

<Analytical Conditions>

| Column: | SUMIPAX ODS D series |
| --- | --- |
| | 5 µm, 4.6 mmφ × 250 mm |
| Mobile phase: | acetonitrile/water = 55/45 |
| Flow rate: | 1.0 ml/min |
| Measurement wavelength: | 240 nm (UV) |
| Temperature: | 40° C. |
| Injection amount: | 1 µl |

Production Example of Derivative (2)>

The content of a carbonyl compound in an air sample can be determined by quantifying a derivative (2) obtained by reaction of a carbonyl compound and a mineral acid salt of a benzylhydroxyamine-based compound (1). A production example of a derivative (2) necessary for this quantification will be illustrated according to the following formulae.

Formulation $C_{30}H_{39}N_6O_{10}P$

Theoretical value: C; 41.5%, H; 4.9%, C; 9.7%. Analytical value: C; 41.2%, H: 5.1%, C; 9.6%.

$^1$H-NMR (δ, ppm, DMSO-d$_6$) . . . 1.36 (9H, t), 4.10 (6H, q), 4.66 (6H. s), 7.35 (3H, d), 7.36 (3H, s), 7.48 (3H, d)

Synthesis Example of (3-1a)>

O-(4-cyano-2-ethoxybenzyl)hydroxyamine hydrochloride (19-1, 2.7 g, 0.012 mol), methanol (20 ml) and water (20 ml) were charged, and a 36% formaldehyde aqueous solution was added to this, and the mixture was stirred at room temperature for 2.0 hours. Water was added to the mixture and the mixture was extracted with ethyl acetate. The resulted ethyl acetate layer was dried over anhydrous magnesium sulfate, then, the solvent was distilled off under reduce pressure. This was purified by silica gel column chromatography using hexane/ethyl acetate system, to obtain O-(4-cyano-2-ethoxybenzyl)hydroxyamine-formaldehyde derivative (3-1a, 2.2 g, yield 96%).

$^1$H-NMR ($\delta$, ppm, CDCl$_3$) ... 1.45 (3H, t), 4.06 (2H, g), 5.21 (2H, s), 6.51 (1H, q), 7.05 to 7.50 (3H, m)

Synthesis Example of (3-1b)>

A derivative (mixture of syn body and anti body) (3-1b, 660 mg, yield 64%) was obtained in the same manner as for the derivative (3-1a) except that acetaldehyde was used.

$^1$H-NMR ($\delta$, ppm, CDCl$_3$) ... 1.44 (3H, t), 1.86 and 1.93 (3H, d), 4.05 (2H, q), 5.13 and 5.20 (2H, s), 6.83 and 7.54 (1H, g), 7.04 to 7.48 (3H, m)

Synthesis Example of (3-1c)>

A derivative (3-1c, 400 mg, yield 78%) was obtained in the same manner as for the derivative (3-1a) except that acetone was used.

$^1$H-NMR ($\delta$, ppm, CDCl$_3$) ... 1.43 (3H, t), 1.89 (3H, s), 1.96 (3H, s), 4.05 (2H, q), 5.15 (2H, s), 7.04 to 7.43 (3H, m)

Synthesis Example of (3-1d)>

A derivative (mixture of syn body and anti body) (3-1d, 450 mg, yield 89%) was obtained in the same manner as for the derivative (3-1a) except that acrolein was used.

$^1$H-NMR ($\delta$, ppm, CDCl$_3$) ... 1.44 (3H, t), 4.05 (2H, q), 5.20 and 5.23 (2H, s), 5.55 and 5.63 (2H, d and s), 6.34 to 6.48 (1H, m), 7.04 to 7.45 (3H, m), 7.84 (1H, d)

Synthesis Example of (3-1e)>

A derivative (mixture of syn body and anti body) (3-1e, 400 mg, yield55%) was obtained in the same manner as for the derivative (3-1a) except that benzaldehyde was used.

$^1$H-NMR ($\delta$, ppm, CDCl$_3$) ... 1.46 (3H, t), 4.08 (2H, q), 5.30 and 5.35 (2H, s), 7.08 and 8.20 (1H, s), 7.23 to 7.61 (8H, m)

Example 1

<Measurement of Blank Value>

Through the carbonyl compound collecting tube obtained above, acetonitrile (5 ml) was passed to cause elution thereof, and 20 µl of the resulted solution was analyzed by liquid chromatography in the same manner as for the O-(4-cyano-2-ethoxybenzyl )hydroxyamine (18). Separately, an amount quantified as blank value was determined as a sample 1 according to an absolute calibration curve method using the above-mentioned derivatives (3-1a), (3-1b) and (3-1c) as a standard. Likewise, quantification was conducted in the same manner also on different 9 carbonyl compound collecting tubes (samples 2 to 10), and the results are summarized in Table 1 together with the sample 1.

The variation coefficient is a scale (% indication) for evaluating substantial extent of dispersion of data by dividing standard deviation by average value, and lower the variation coefficient, smaller the dispersion of measured values.

Table 1 shows the measured results and FIG. 2 (1) shows a typical chart of Table 1. For reference, FIG. 2 (2) shows a chart of samples containing each derivative of O-(4-cyano-2-ethoxybenzyl)hydroxyamine (18) containing 0.5 µg/ml of formaldehyde, acetaldehyde, acetone and acrolein.

TABLE 1

| Sample | HCHO (µg/tube) | CH$_3$CHO(µg/tube) |
|---|---|---|
| 1 | 0.0022 | 0.0016 |
| 2 | 0.0020 | 0.0019 |
| 3 | 0.0021 | 0.0018 |
| 4 | 0.0018 | 0.0023 |
| 5 | 0.0020 | 0.0023 |
| 6 | 0.0020 | 0.0021 |
| 7 | 0.0018 | 0.0015 |
| 8 | 0.0020 | 0.0023 |
| 9 | 0.0021 | 0.0022 |
| 10 | 0.0023 | 0.0019 |
| average | 0.0020 | 0.0019 |
| variation coefficient | 7.7 | 14.9 |

The samples 1 to 10 showed no peak of derivatives of carbonyl compounds other than formaldehyde, acetaldehyde and acetone. Further, it was clarified that blank value is low and dispersion thereof is small in the case of formaldehyde and acetaldehyde. It was also clarified that though acetone shows higher value as compared with formaldehyde and acetaldehyde, it has smaller dispersion.

Comparative Example 1

<Blank Value of DNPH Collecting Tube>

Ten blank values of DNPH sampler short body (formaldehyde scavenger manufactured by Waters, containing 2,4-dinitrophenylhydrazine (DNPH))were quantified in the same manner as in Example 1. The DNPH-formaldehyde derivative, DNPH-acetaldehyde derivative and DNPH-acetone derivative are all marketed from Sigma Aldrich, and these were used. The results are shown in Table 2, and FIG. 3 (1) shows a typical chart of Table 2. For reference. FIG. 3 (3) shows a chart of samples containing each derivative of DNPH contained in an amount of 0.5 µg/ml as a concentration of formaldehyde, acetaldehyde and acetone.

TABLE 2

| Sample | HCHO (µg/tube) | CH$_3$CHO(µg/tube) |
|---|---|---|
| 1 | 0.0336 | 0.0447 |
| 2 | 0.0255 | 0.2079 |
| 3 | 0.0348 | 0.0471 |
| 4 | 0.0291 | 0.2211 |
| 5 | 0.0390 | 0.0516 |
| 6 | 0.0495 | 0.0477 |
| 7 | 0.0378 | 0.0543 |
| 8 | 0.0333 | 0.1716 |
| 9 | 0.0321 | 0.0543 |
| 10 | 0.0321 | 0.0333 |
| average | 0.0347 | 0.0934 |
| variation coefficient | 18.7 | 80.3 |

Figure 2A:
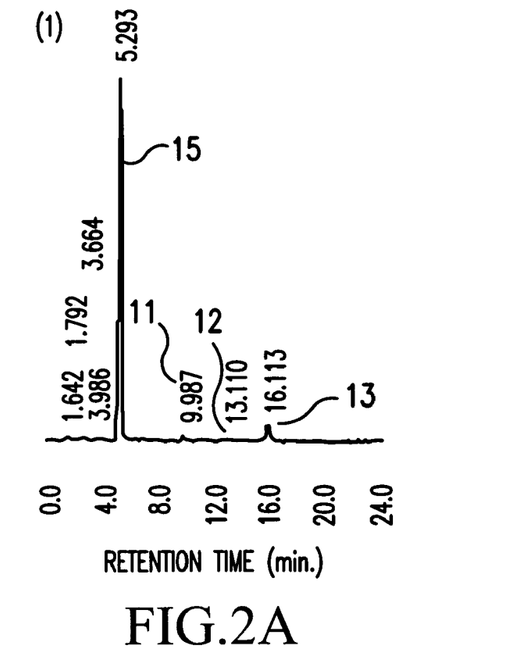
Figure 2B:
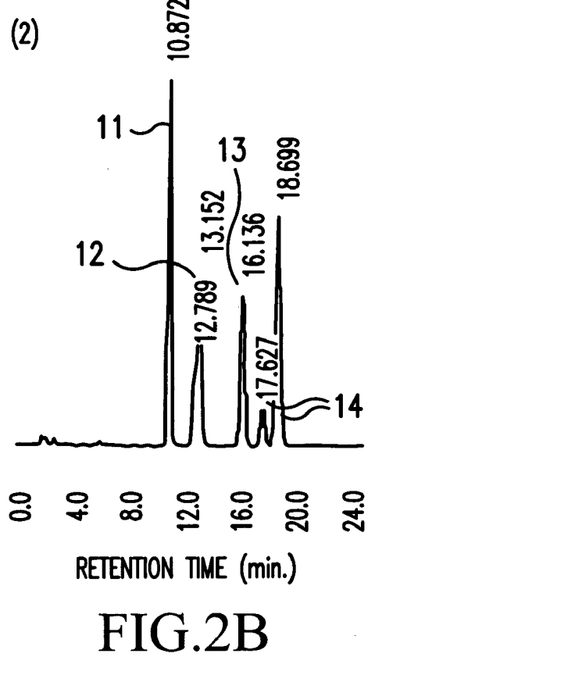
Figure 3A:
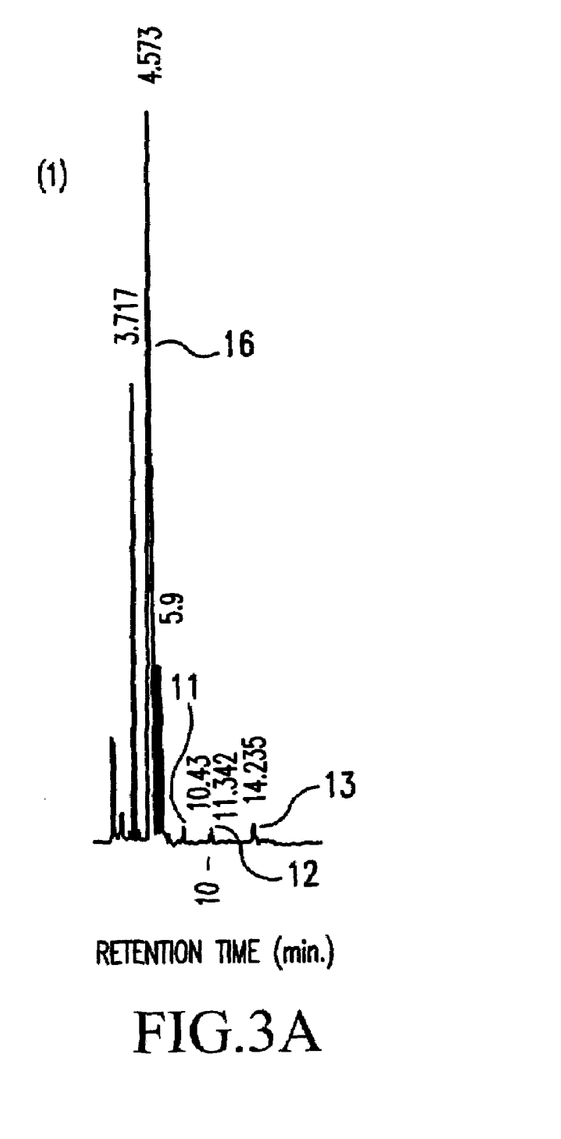
Figure 3B:
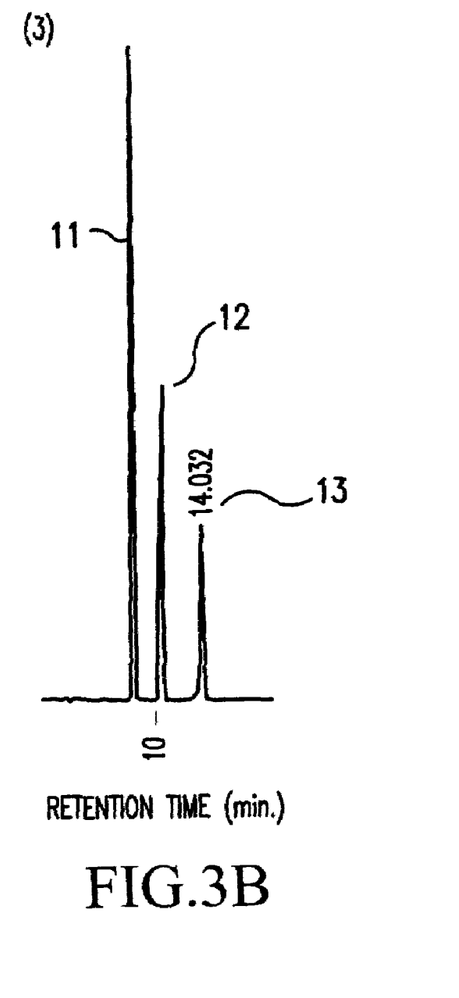

In the case of a scavenger containing DNPH, blank values of formaldehyde and acetaldehyde are higher 15 times or more as compared with the collecting tube in Example 1and the variation coefficient is also larger. Also from comparison of blank charts of FIGS. 2 and 3, it is known that the carbonyl compound scavenger of the present invention shows smaller number of other detectable blank peaks as compared with scavengers containing DNPH.

Example 2

<Collecting Test by Formaldehyde Standard Gas>

Formaldehyde generated by thermally decomposing p-formaldehyde using a standard gas generator manufactured by Gasteck was diluted at constant flow rate from an air bomb of high purity, to prepare air samples 1 to 6 of which gas concentration was controlled at approximately 20 to 350 ppb. Two of the above-mentioned carbonyl compound collecting tubes were connected and the air sample was collected for 30 minutes at a rate of 500 ml/min. After collection, acetonitrile (5 ml) was passed through each collecting tube to elute a formaldehyde derivative, and the resulted solution was quantified in the same manner as in Example 1.

The results of the air samples 1 to 6 are summarized in Table 3.

TABLE 3

| Air sample | Concentration of HCHO generated[1] (ppb) | Sampler HCHO concentration at first stage (ppb) | Sampler HCHO concentration at second stage (ppb) | collecting efficiency[2] (%) |
|---|---|---|---|---|
| 1 | 20.2 | 20.4 | 0 | 101 |
| 2 | 64.6 | 64.8 | 0 | 100 |
| 3 | 96.0 | 97.3 | 0 | 101 |
| 4 | 160.7 | 163.3 | 0 | 102 |
| 5 | 198.2 | 200.2 | 0 | 101 |
| 6 | 347.5 | 346.6 | 0 | 99.7 |

[1] formaldehyde concentration quantified by DNPH sampler manufactured by Waters
[2] collecting efficiency of total value at first stage and second stage of sampler, when the concentration generated is 100

The formaldehyde collecting test results in Table 3 show that all aldehydes are collected at the first stage and excellent results are obtained from lower concentrations around 20 ppb to higher concentrations around 350 ppb.

Example 3

<Heat Resistance Test of Formaldehyde Derivative>

Into the carbonyl compound collecting tube used in Example 1 the O-(4-cyano-2-ethoxybenzyl)hydroxyamine-formaldehyde derivative (3-1a) of approximately 1 μg as a formaldehyde amount was injected to prepare 7 collecting tubes, and one (time: 0 min) of them was used to elute a derivative (3) in the same manner as in Example 1 and the collecting amount as a formaldehyde was determined. Other collecting tubes were allowed to stand still for times described in Table 4 in a high temperature bath of 80° C., and the amount of a derivative was quantified. The derivative was quantified in terms of formaldehyde and the results are shown in Table 4.

The results in Table 4 teach that in all of the carbonyl compound collecting tubes, a derivative corresponding to approximately 1 μg as a formaldehyde is collected, that is, the carbonyl compound scavenger of the present invention can collect a carbonyl compound stably at least for 90 minutes at 80° C.

TABLE 4

| Time (minute) | HCHO amount in sampler (μg) |
|---|---|
| 0 | 1.02 |
| 10 | 1.08 |
| 20 | 1.10 |
| 30 | 1.05 |
| 45 | 1.02 |

TABLE 4-continued

| Time (minute) | HCHO amount in sampler (μg) |
|---|---|
| 60 | 1.05 |
| 90 | 1.06 |

Example 4

<Measurement of Formaldehyde in Air Sample in General Dwelling Environment>

Using the carbonyl compound scavenger obtained in Example 1 room airs in three rooms of an actual general dwelling house were collected at approximately 25° C. for 30 minutes at a collecting flow rate of 500 ml/min, eluted, then, quantified by liquid chromatography. The results are shown in Table 5 together with the result in the case of use of DNPH sampler short body (manufactured by Waters) as a collecting tube.

As apparent from Table 5 the carbonyl compound scavenger of the present invention shows approximately the equivalent measured concentration to that of a scavenger containing DNPH as a standard, also on air samples such as room airs in general dwelling houses in which various gases are present.

TABLE 5

| Room | Example 4 HCHO (ppb) | HCHO concentration (ppb) by DNPH |
|---|---|---|
| 1 | 62 | 63 |
| 2 | 62 | 64 |
| 3 | 101 | 91 |

Reference Example 1

<Measurement of Formaldehyde in Air Sample in General Dwelling Environments Using Carbonyl Compound Scavenger Containing PFBOA>

2.5 mg of O-(2,3,4,5,6-pentafluorobenzyl)hydroxyamine (PFBOA) (manufactured by Hayashi Junyaku Kogyo K. K.) was coated on Bond Elute Junior SCX (manufactured by Varian Co.) to produce a collecting tube, and room airs in three rooms of an actual dwelling house different from that in Example 4 were collected at approximately 25 to 30° C. for 30 minutes at a collecting flow rate of 330 ml/min, eluted, then, quantified by GC/MS (SIM). The results are shown in Table 6 together with the result in the case of use of DNPH sampler short body (manufactured by Waters) as a collecting tube.

Table 6 clarified that the collecting efficiency of PFBOA remains only 70 to 77% as compared with collecting tubes containing DNPH at 25 to 30° C.

TABLE 6

| Room | Reference Example 1 HCHO (ppb) | HCHO concentration (ppb) by DNPH |
|---|---|---|
| 1 | 72 | 93 |
| 2 | 67 | 89 |
| 3 | 57 | 81 |

As the derivative of PFBOA and formaldehyde, a standard article of Hayashi Junyaku Kogyo K. K. was used, and the conditions for GC/MS (SIM) are as shown below.

<GC/MS Measurement Conditions>

| | |
|---|---|
| Instrument: | HP 6890/5972A type gas chromatography mass analyzer |
| Column: | J&W DB-1 (0.25 μm) 0.25 mmø × 30 m |
| Injection temperature: | 250° C. |
| Detector temperature: | 280° C. |
| Column: | 50° C. (10 minutes) → (10° C./min) → 250° C. (0 minute) |
| Split Rate: | 1/30 |
| Carrier Gas: | He 1.0 ml/min |
| Measurement mode: | SIM method |
| Measured mass number (m/z): | formaldehyde 181 |
| Injection amount: | 1 μl was injected |

Example 5

<Collecting Test by Passive Sampler>

The carbonyl compound scavenger (300 mg) in Example 1 was filled in a porous cylindrical tube (diameter 7 mm, length 40 mm) to obtain a porous cylindrical tube type passive, then, coated with an aluminum laminate to avoid contact with an outer gas. Next, into a glass vessel for thin layer chromatography (longitudinal×lateral×height=20×8× 21 cm) was added 0.5 ml of a commercially available 36% formaldehyde aqueous solution (manufactured by Wako Pure Chemical Ltd.), and closely sealed for a while.

Two hours after, the above-mentioned porous cylindrical tube type passive was placed and closely sealed and left for 4 hours, then, all the amount of the filled substance in the porous cylindrical tube passive was released into a screw tube made of glass and acetonitrile (5 ml) was added to this and the mixture was stirred and left for a while. The supernatant thereof was analyzed by liquid chromatography in the same manner as in Example 1. As a result, formaldehyde was collected in an amount of 176.6 μg as an average value of three samples.

What is claimed is:

1. A carbonyl compound scavenger comprising a mineral acid salt of a benzylhydroxyamine-based compound of the formula (1) and at least one adsorbent selected from the group consisting of silica gel, alumina, cellulose and activated carbon:

(1)

wherein, R represents an alkyl group having 1 to 8 carbon atoms, haloalkyl group having 1 to 4 carbon atoms, alkoxy group having 1 to 4 carbon atoms, haloalkoxy group having 1 to 4 carbon atoms, nitro group or cyano group, and $R^1$ and $R^2$ represent each independently a hydrogen atom or alkyl group having 1 to 8 carbon atoms, and a hydrogen atom on a benzene ring to which a cyano group and R are connected may be substituted with an alkyl group having 1 to 8 carbon atoms, haloalkyl group having 1 to 4 carbon atoms, alkoxy group having 1 to 4 carbon atoms, haloalkoxy group having 1 to 4 carbon atoms, aryl group having 6 to 10 carbon atoms, nitro group or cyano group.

2. A carbonyl compound scavenger obtained by compounding a benzylhydroxyamine-based compound of the formula (1), a mineral acid salt and at least one adsorbent selected from the group consisting of silica gel, alumina, cellulose and activated carbon:

(1)

wherein, R represents an alkyl group having 1 to 8 carbon atoms, haloalkyl group having 1 to 4 carbon atoms, alkoxy group having 1 to 4 carbon atoms, haloalkoxy group having 1 to 4 carbon atoms, nitro group or cyano group, and $R^1$ and $R^2$ represent each independently a hydrogen atom or alkyl group having 1 to 8 carbon atoms, and a hydrogen atom on a benzene ring to which a cyano group and R are connected may be substituted with an alkyl group having 1 to 8 carbon atoms, haloalkyl group having 1 to 4 carbon atoms, alkoxy group having 1 to 4 carbon atoms, haloalkoxy group having 1 to 4 carbon atoms, aryl group having 6 to 10 carbon atoms, nitro group or cyano group.

3. The carbonyl compound scavenger according to claim 1 or 2, wherein the mineral acid is phosphoric acid.

4. The carbonyl compound scavenger according to claim 1, wherein the adsorbent is silica gel for chromatography.

5. A collecting tube comprising a vessel having air permeability filled with the carbonyl compound scavenger according to claim 1.

6. A carbonyl compound quantification kit comprising the collecting tube according to claim 5 sealed with a non-air permeable material.

7. A method for quantifying a carbonyl compound comprising the steps of:

washing the scavenger according to claim 1 with at least one hydrophilic solvent selected from the group consisting of lower aliphatic nitriles, lower alcohols, lower aliphatic ethers and lower cyclic ethers, drying this, allowing a sample containing a carbonyl compound of the formula:

$R^3C(=O)R^4$ (wherein $R^3$ and $R^4$ represent each independently a hydrogen atom, alkyl group having 1 to 8 carbon atoms, alkenyl group having 1 to 8 carbon atoms or aryl group having 6 to 10 carbon atoms) to permeate through the resulted scavenger to adsorb the carbonyl compound as a derivative of the formula (2), subsequently, washing with a hydrophilic solvent to elute the derivative (2), and quantifying the derivative (2) in the resulting washing liquid:

(2)

wherein, R, $R^1$, $R^2$, $R^3$ and $R^4$ represent the same meanings as described above.

* * * * *